United States Patent
Pei et al.

(10) Patent No.: US 7,308,307 B1
(45) Date of Patent: Dec. 11, 2007

(54) IMPLANTABLE SINGLE-CHAMBER ATRIAL PACING DEVICE PROVIDING ACTIVE VENTRICULAR FAR FIELD SENSING AND RATE LIMIT

(75) Inventors: Xing Pei, Thousand Oaks, CA (US); Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 547 days.

(21) Appl. No.: 10/792,207

(22) Filed: Mar. 2, 2004

(51) Int. Cl.
*A61N 1/365* (2006.01)

(52) U.S. Cl. ............... 607/9; 607/17; 607/25
(58) Field of Classification Search ............ 607/9, 607/14, 17, 25
See application file for complete search history.

(56) References Cited

U.S. PATENT DOCUMENTS

| | | | | |
|---|---|---|---|---|
| 4,523,593 | A * | 6/1985 | Rueter | 607/9 |
| 4,788,980 | A * | 12/1988 | Mann et al. | 607/14 |
| 5,334,220 | A * | 8/1994 | Sholder | 607/9 |
| 5,470,342 | A * | 11/1995 | Mann et al. | 607/5 |
| 5,643,326 | A * | 7/1997 | Weiner et al. | 607/14 |
| 5,741,308 | A * | 4/1998 | Sholder | 607/9 |
| 5,999,853 | A * | 12/1999 | Stoop et al. | 607/9 |
| 6,101,416 | A * | 8/2000 | Sloman | 607/28 |
| 6,128,529 | A * | 10/2000 | Esler | 607/4 |
| 6,434,428 | B1 | 8/2002 | Sloman et al. | 607/28 |
| 6,477,416 | B1 * | 11/2002 | Florio et al. | 607/9 |
| 6,516,225 | B1 | 2/2003 | Florio | 607/9 |
| 6,526,311 | B2 | 2/2003 | Begemann | 600/509 |
| 6,539,259 | B1 * | 3/2003 | Weinberg et al. | 607/9 |
| 6,711,438 | B1 * | 3/2004 | McClure et al. | 607/9 |
| 6,788,971 | B1 * | 9/2004 | Sloman et al. | 607/28 |
| 6,862,471 | B1 * | 3/2005 | McClure et al. | 600/509 |
| 6,873,875 | B1 * | 3/2005 | Gilkerson et al. | 607/9 |
| 6,944,499 | B2 * | 9/2005 | Tang et al. | 607/9 |
| 7,024,243 | B1 * | 4/2006 | Bornzin et al. | 607/14 |

* cited by examiner

*Primary Examiner*—Kristen D. Mullen
*Assistant Examiner*—Eugene T Wu

(57) ABSTRACT

A maximum pacing rate is dynamically established during single-chamber atrial pacing of a heart by a rate control system within a single-chamber or dual-chamber cardiac stimulation device which paces the atria of a heart on demand at the end of an escape interval. The system includes a detector that detects an atrial activation of the heart and an R wave of the heart corresponding to the detected atrial activation. The system further includes a rate limit circuit that determines a minimum RA interval and extends the escape interval to an extended escape interval to end with the minimum RA interval.

23 Claims, 4 Drawing Sheets

IMPLANTABLE SINGLE-CHAMBER ATRIAL PACING DEVICE PROVIDING ACTIVE VENTRICULAR FAR FIELD SENSING AND RATE LIMIT

FIELD OF THE INVENTION

The present invention generally relates to an implantable cardiac device. The present invention more particularly relates to an implantable single-chamber atrial pacemaker capable of active ventricular far field sensing and rate limiting.

BACKGROUND

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system applies pacing pulses to and senses cardiac activity in only one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Single chamber atrial pacing with either a single-chamber or dual-chamber device provides atrial pacing when required during atrial bradycardia. It is used in patients that have intact AV conduction. The resulting atrial synchrony enables ventricular activity to track atrial activity to more closely approximate normal response to exercise or other physiological activity.

Many pacemakers incorporate a physiologic sensor. Such sensors are employed to detect the patient's degree of activity for regulating the heart rate. Hence, as the patient becomes more active, requiring increased cardiac output, the stimulation rate of the pacemaker is increased. When the patient becomes less active, requiring reduced cardiac output, the stimulation rate of the pacemaker is in turn decreased.

Single-chamber atrial pacemakers implement two main timing intervals to support their operation. These intervals are referred to as the refractory period and the atrial escape interval. The refractory period is the time from an atrial pacing pulse or a detected P wave to after the T wave of the ventricle. During this time, the device will not respond to sensed activity to prevent a far field R wave or T wave from being detected as an intrinsic P wave.

The atrial escape interval is the time from a detected P wave or an atrial pacing pulse to when a next atrial pacing pulse is to be delivered absent a preoccurring P wave. This pacing is referred to as atrial demand pacing.

Sensing of far field ventricular activations (R wave) in a single atrial channel is a major problem in single-chamber atrial devices or in dual-chamber devices operating in a single chamber atrial pacing mode. In such devices, it is not easy to distinguish far field ventricular activations from true atrial activity because these devices do not utilize a ventricular channel. Traditionally, such devices utilize various methods in an effort to minimize the impact of the sensing of the far field activity. These methods include refractory time, rate modulated refractory time, or absolute refractory time, for example. All these methods attempt to block the far field ventricular signal or treat it as a signal which should be discarded. If the device fails to block the far field ventricular signal, the signal can then inhibit the pacing of the device and result in a non-output condition when an output may be required.

The amplitude and timing of the far field ventricular signal generally vary with lead location and AV node conduction sufficiency, which is modulated by neurotransmitters. This makes it difficult to determine the proper refractory time to be used. The AV conduction also depends upon whether there is an intrinsic atrial event or a paced atrial event. The difference can be dramatic. Incorrect sensing of far field ventricular events can lead to an incorrect diagnosis and/or a failure to deliver therapy. In addition, pacing induced heart block can result from increased pacing rate, particularly with modern atrial over-drive therapy where the AV node conduction may not be able to accommodate the pacing rate increases demanded by the therapy.

Thus, the present invention addresses these issues in order to fully utilize the advantages of single-chamber atrial pacing devices and the atrial pacing therapies obtainable therewith.

As will be seen hereinafter, the invention provides a device and method which utilizes active searching for far field ventricular activity to enable the proper atrial refractory time to be determined dynamically and an upper pacing rate limit to be established.

SUMMARY

What is described herein is a system for dynamically establishing a maximum pacing rate for use in a cardiac stimulation device which paces the atria of a heart on demand at the end of an escape interval in a single-chamber atrial pacing mode. The system comprises a detector that detects an atrial activation of the heart and an R wave of the heart corresponding to the detected atrial activation, and a rate limit circuit that imposes a minimum RA interval on the escape interval. The rate limit circuit varies the minimum RA interval responsive to pacing rate.

The device may be either a single-chamber or a dual-chamber cardiac device. If the device is a single-chamber device, the R wave is a far field R wave detected with an atrial sense channel. If the device is a dual-chamber device, the R wave may be detected with either a ventricular sense channel as a near field R wave or an atrial sense channel as a far field R wave.

The system may further comprise a blanking circuit that disables detection by the detector during a blanking interval commencing with detection of the atrial activation and ending prior to detection of the R wave.

The blanking interval may have a first duration responsive to an intrinsic atrial activation and a second duration responsive to a paced atrial activation. The first duration is preferably shorter than the second duration.

The device may include a refractory circuit that provides a refractory period following detection of the atrial activation and the system may further comprise a refractory control that sets a revised refractory period responsive to detection of the R wave.

The system may further comprise a morphology detector that confirms detection of the R wave. The system may further comprise a blanking circuit that disables detection by the detector during a blanking period beginning with detection of the R wave and ending after a T wave following the R wave.

In another embodiment, a method of dynamically establishing a maximum pacing rate in a cardiac stimulation device is provided, which paces the atria of a heart on demand at the end of an escape interval in a single-chamber atrial pacing mode. The method comprises detecting an atrial activation of the heart, detecting an R wave of the heart corresponding to the detected atrial activation, determining a minimum RA interval, and imposing the minimum RA interval on the escape interval. The minimum RA interval may be determined based upon pacing rate.

The method may further include the step of blanking detection by the detector during a blanking interval commencing with detection of the atrial activation and ending prior to detection of the R wave. The device may include a refractory circuit that provides a refractory period following detection of the atrial activation and the method may further comprise setting a revised refractory period responsive to detecting the R wave.

The method may further comprise the step of performing morphology analysis to confirm detection of the R wave.

The method may further comprise the step of blanking detection by the detector during a blanking period beginning with detection of the R wave and ending after a T wave following the R wave.

In another embodiment, a system is provided for dynamically establishing a maximum pacing rate for use in a cardiac stimulation device which paces the atria of a heart on demand at the end of an escape interval in a single-chamber atrial pacing mode. The system comprises detecting means for detecting an atrial activation of the heart and an R wave of the heart corresponding to the detected atrial activation, and rate limit means for imposing a minimum RA interval on the escape interval.

BRIEF DESCRIPTION OF THE DRAWINGS

Further features and advantages may be more readily understood by reference to the following description taken in conjunction with the accompanying drawings, in which.

DESCRIPTION OF THE PREFERRED EMBODIMENTS

The following description is of the best mode presently contemplated. This description is not to be taken in a limiting sense but is made merely for the purpose of describing the general principles of the disclosed embodiments. The scope of the invention should be ascertained with reference to the issued claims. In the description that follows, like numerals or reference designators will be used to refer to like parts or elements throughout.

Figure 1:
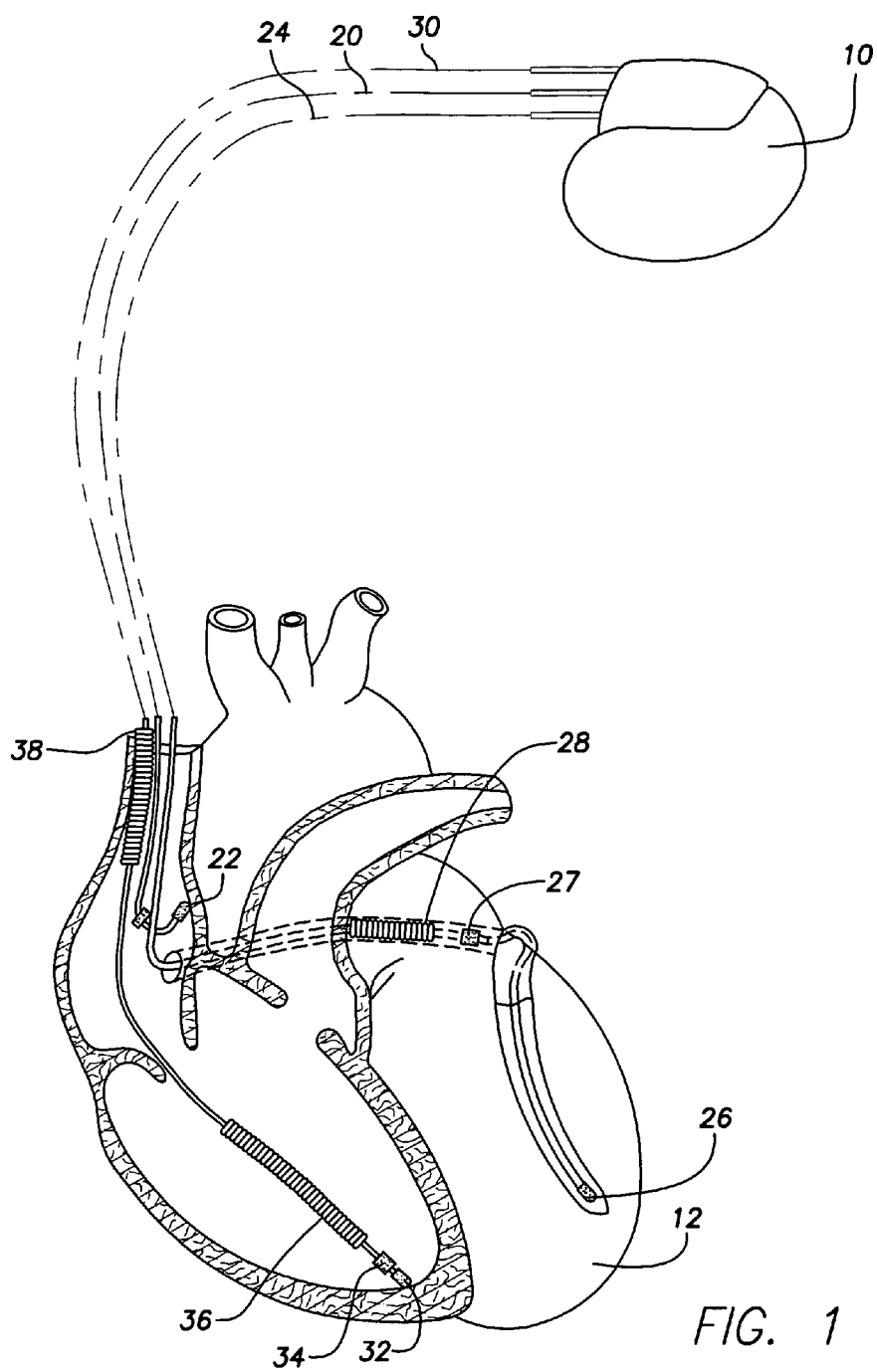
FIG. 1 is a simplified diagram illustrating an implantable stimulation device shown in electrical communication with at least three leads implanted into a patient's heart for delivering single-chamber or multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The lead 20 may further include a ring electrode 23 for supporting bipolar sensing and atrial stimulation.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
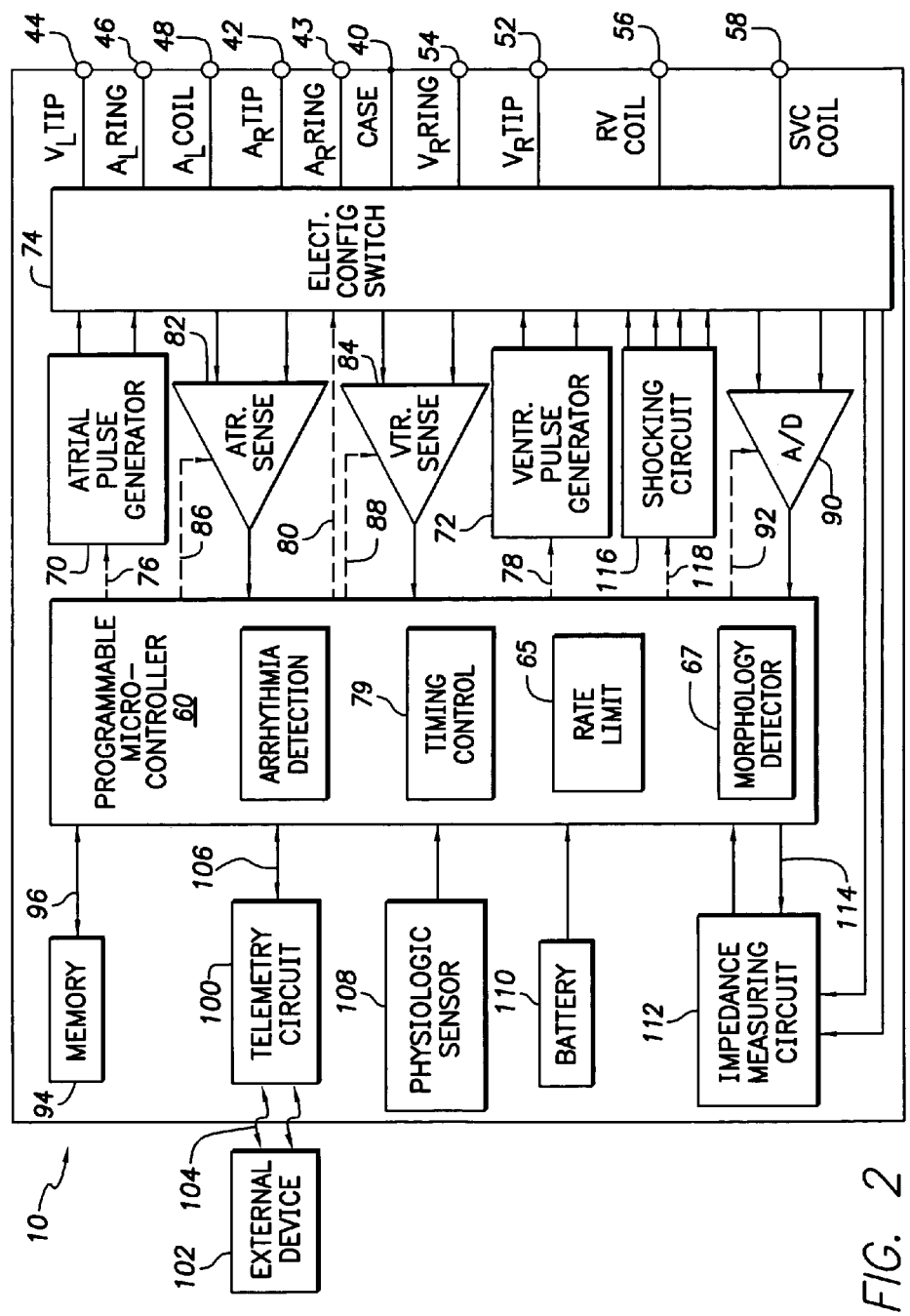
FIG. 2 is a functional block diagram of the device of FIG. 1.

As illustrated in FIG. 2, a simplified block diagram is shown of the implantable stimulation device 10, which is capable of treating both fast and slow arrhythmias with stimulation therapy, including cardioversion, defibrillation, and pacing stimulation. While a particular multi-chamber device is shown, this is for completeness only, and one of skill in the art could readily appreciate that the illustrated device may be programmed in a single-chamber atrial mode as well. Accordingly, the device 10 is capable of multi-chamber operation but could be substituted with a single-chamber atrial device.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 which may be used with the case 40 for unipolar operation or with an atrial ring terminal ($A_R$ RING) 43 for bipolar operation.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that although the described embodiment is directed to single-chamber atrial pacing, the device may be capable to provide stimulation therapy in each of the four chambers of the heart, and that to that end, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiologic sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the device 10 has been generally described, this discussion will now turn more particularly to this embodiment, which is directed to a rate limit control for use in single-chamber atrial pacing. Switch 74 is preferably set to couple the right atrial tip electrode 22 and the case 40 to the atrial pulse generator 70, the atrial sensing circuit 82 and to the data acquisition system 90. In addition, if R waves are to be sensed as near field R waves, the switch 74 preferably also couples the ventricular sensing circuit 84 to a ventricular electrode configuration such as electrodes 32 and 34 for bipolar ventricular sensing.

To provide the rate limit control, the device includes a rate limit control 65. As will be appreciated by those skilled in the art, the rate limit control 65 may be implemented by the microcontroller 60, as in this embodiment, or by a separate, stand alone circuit.

The rate limit control 65 limits the upper pacing rate dynamically by dynamically imposing a minimum RA interval for each cardiac cycle of the heart. To accomplish this, rate limit control 65 uses active searching for the far field or near field R wave. Once the R wave is detected, the rate limit control imposes, on the escape interval of the device, a minimum RA interval determined dynamically based upon pacing rate.

For purposes of describing the preferred embodiment herein, it shall be assumed that the R wave is being sensed as a far field R wave using an atrial electrode configuration. However, as previously described, the embodiment may also be practiced by sensing R waves as near field R waves and T waves using a ventricular electrode configuration. While the device of FIG. 2 is capable of sensing cardiac activity with either an atrial channel or a ventricular channel, the detection of the R waves as far field R waves and T waves with an atrial electrode configuration is described herein because it represents a general case for either a single-chamber atrial pacing device or a dual-chamber device.

Figure 3:
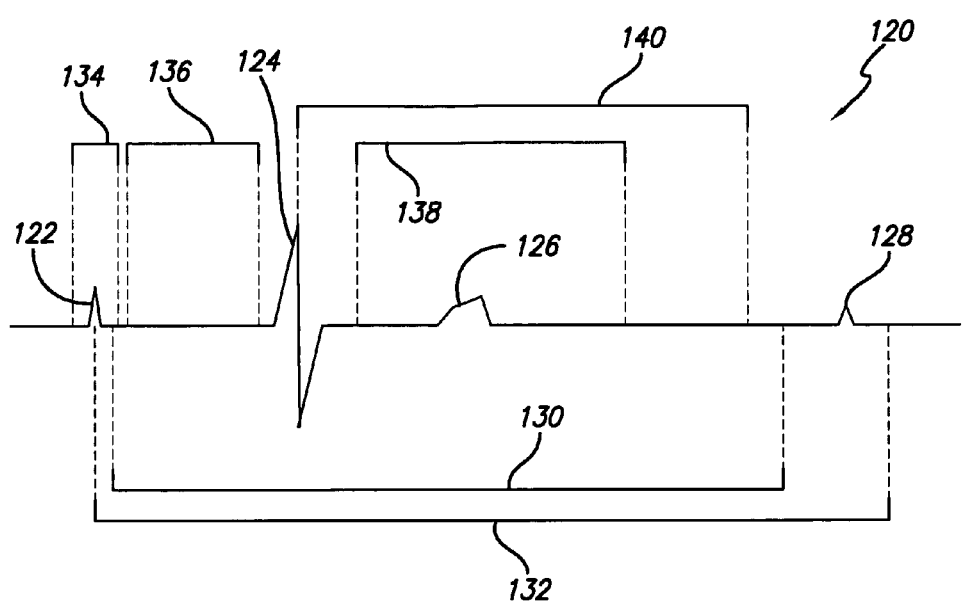
FIG. 3 is an electrogram illustrating various timed periods which may be imposed in accordance with an illustrative embodiment.

FIG. 3 may be referred to for better understanding. In FIG. 3 an electrogram 120 is shown. The more predominate morphological features of the electrogram 120 include a first atrial activation 122, a far field R wave 124, a T wave 126 corresponding to the far field R wave 124, and a second atrial activation 128. The atrial activation 122 may be an intrinsic P wave or an A wave induced by an atrial pacing pulse. The atrial activation 128 shown in FIG. 3 is an intrinsic P wave.

In accordance with this embodiment, the device implements standard single-chamber atrial demand pacing. To that end, upon atrial activation 122, either sensed or paced, the device establishes a refractory period 130 which begins with the activation 122 and normally terminates before the next expected atrial activation 128. During this interval, the device may continue to sense cardiac activity with the atrial channel but will not take any action in response thereto.

Another interval established by the device 10 is the escape interval 132. This interval also begins with the atrial activation 122. It continues up to a time when an atrial stimulation pulse is to be delivered for pacing the atria. However, if an intrinsic P wave is sensed, such as P wave 128, before the escape interval expires, the pacing pulse is inhibited and new refractory and escape intervals are begun. The refractory and escape intervals may be dynamic based on cardiac rate as is known in the art.

As will be seen subsequently, additional intervals are timed or may be timed in accordance with the present embodiment. The first such interval is a cross channel blanking interval 134 which is begun with an atrial pacing pulse and timed for a short period of time to enable noise caused by the pacing pulse to subside.

Following the cross channel blanking interval, if there is one, or with the detection of an intrinsic P wave, the device begins a minimum conduction delay 136 which is a blanking period wherein no cardiac activity is sensed. The length of this blanking interval 136 is chosen so as to terminate before far field R wave 124 is expected to be sensed. Since the AV conduction times for intrinsic P wave and paced A waves are usually different, this interval may be different for these two conditions. More particularly, the AV conduction delay for intrinsic P waves is generally shorter than that for paced A waves. For example, the AV conduction delay for intrinsic P waves may be on the order of 75 ms (milliseconds), for example, whereas the AV conduction delay for paced A waves may be on the order of 150 ms, for example. In addition, the conduction delay 136 will also change dynamically with cardiac rate. Thus, it is preferred that the interval 136 also be dynamically varied with cardiac rate.

Once the blanking interval 136 ends, a window is opened for actively sensing the far field R wave 124. If the far field R wave is sensed, the device then takes control of the normal refractory period 130 and sets a revised refractory period 138 which begins after the sensing of the far field R wave and ends after the expected T wave 126 but before what would have been the end of the original refractory period 130. The refractory period 138 may be set to end sooner (as shown) or later than the refractory period 130 depending on the location, in time, of the far field R wave and thus the predicted location, in time, of the resulting T wave and the cardiac rate at that time.

Lastly, with the sensing of the far field R wave, minimum RA interval 140 is imposed on the escape interval. Hence, if the escape interval as determined by rate response or an atrial overdrive protocol is scheduled to end before the end of the minimum RA interval, the escape interval is extended to end at the end of the minimum RA interval 140. In this manner, the atrial pacing rate is dynamically limited and may be controlled to permit completion of the atrial conduction interval regardless of the dictated escape interval. This assures reliable pacing support at all times.

The revised refractory interval 138 and the minimum RA interval may both be dynamically controlled based upon the varying cardiac or pacing rate. Hence, if the patient is exercising, the upper rate limit will be high, but if the patient is at rest, the upper rate limit will be dynamically lowered. Measures for dynamically adjusting such intervals as the revised refractory interval 138 and minimum RA interval 140 are well known in the art. Of course, the escape interval 132 and conduction delay 136 may also be rate modulated as is known in the art.

As a further feature, the data acquisition system 90 may be employed for confirming detection of the far field R wave. This elective measure would include the collection of digital data representing the sensed cardiac activity, storing the same in memory 94, and then performing a morphology analysis with the data by the morphology detector 67. Such analysis may include, for example, matching the stored electrogram to a template and determining the degree of match. Such template matching is well known in the art. If the result is positive, the far field R wave may be considered to have been detected. If the result is negative, searching for the far field R wave is continued.

Should the far field R wave not be detected, the original refractory period is imposed. Upon subsequent time out of the escape interval, a pacing pulse is applied. The pacing pulse is alternatively inhibited if an intrinsic P wave is detected after the refractory period and before time out of the escape interval.

Figure 4:
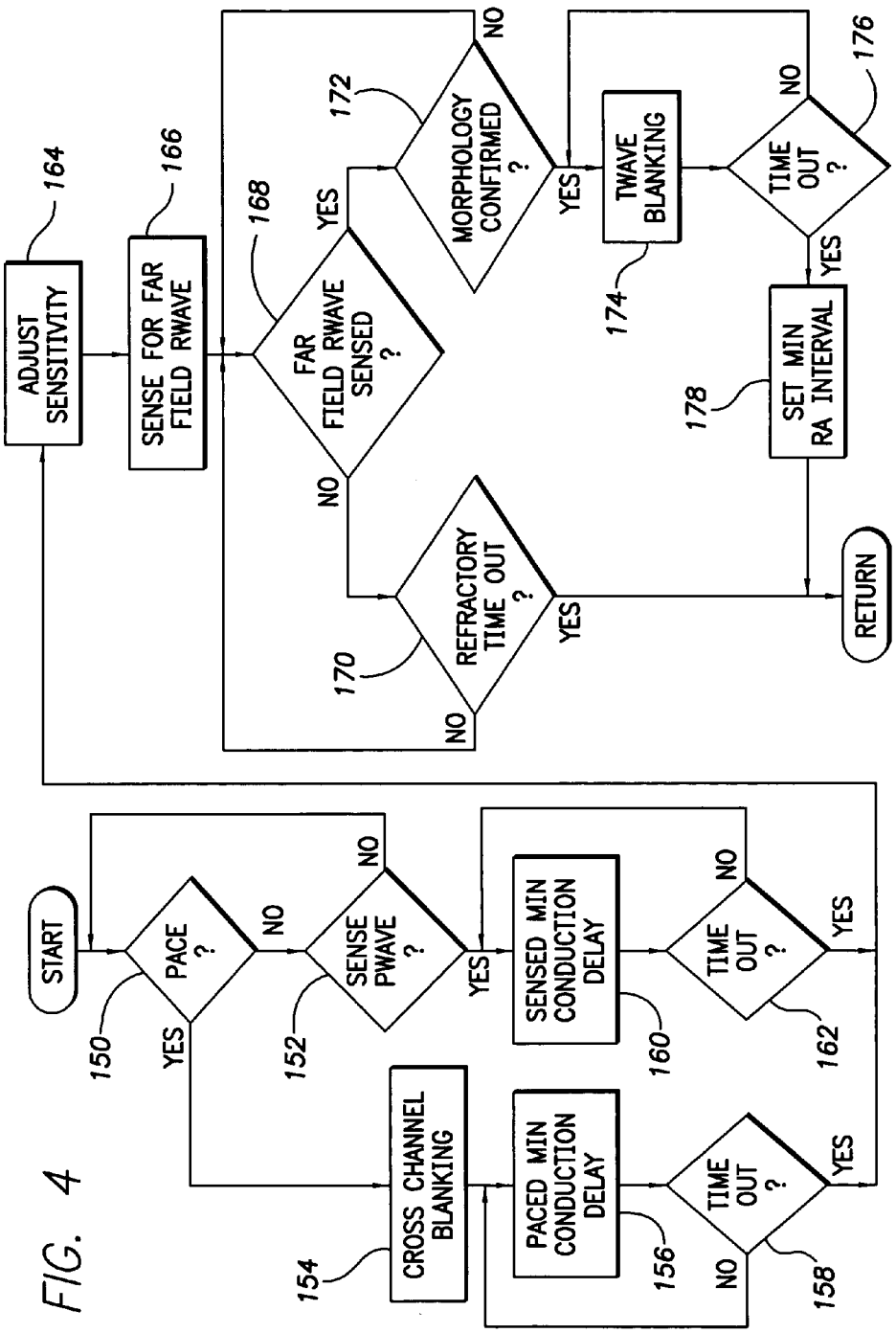
FIG. 4 is a flow chart describing an overview of the operation of one embodiment.

The foregoing is more particularly summarized in the flow diagram of FIG. 4. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 4 initiates with decision block 150. In decision block 150, the rate limit control 65 determines if the device has issued a pacing pulse. If the device has not issued a pacing pulse, the process advances to decision block 152 wherein the rate limit control determines if an intrinsic P wave has been sensed. If an intrinsic P wave has not been sensed, the process returns to decision block 150. However, if in decision block 150 it is determined that the device has delivered an atrial pacing pulse, the process advances to activity block 154. In activity block 154, the device provides the cross-channel blanking period 134. After the cross-channel blanking period, the process advances to activity block 156 where the device begins timing of the paced minimum conduction delay 136. As previously described, the paced minimum conduction delay 136 may be on the order of 150 milliseconds and dynamically determined based upon cardiac rate. In decision block 158, the rate limit control determines when the paced minimum conduction delay has timed out. When it times out, the process advances to activity block 164 to be described subsequently.

If in decision block 152 it is determined that an intrinsic P wave has been sensed, the process then advances to activity block 160 wherein the rate limit control implements the sensed minimum conduction delay. As previously mentioned, the sensed minimum conduction delay may be on the order of 75 milliseconds and dynamically determined based upon cardiac rate. During the timing of the sensed minimum conduction delay, the rate limit control 65 implements decision block 162 to determine when the sensed minimum conduction delay times out. When it times out, the process then advances to activity block 164. With the timing out of either paced minimum conduction delay or the sensed minimum conduction delay, the window is opened for actively searching for the far field R wave. First, in accordance with activity block 164, the sensitivity of the atrial channel is adjusted to accommodate the expected signal level of the far field R wave. Once the sensitivity has been adjusted, the process advances to activity block 166 where sensing begins for the far field R wave. During activity block 166, decision block 168 is implemented by the rate limit control 65 to determine if the far field R wave has been sensed. If the far field R wave has not been sensed, the process advances to decision block 170 to determine if the original refractory period 130 has timed out. If the original refractory period has not timed out, the process continues to determine if a far field R wave has been sensed. If the far field R wave is not sensed before the refractory period times out, the process returns. Normal atrial pacing ensues such that upon expiration of the escape interval, an atrial pacing pulse is provided by the device. If, however, an intrinsic P wave is detected after the end of the original refractory period and before expiration of the escape interval, the pacing pulse is inhibited and a new regular refractory period is begun.

If in decision block 168 it is determined that the far field R wave 124 has been sensed before the expiration of the original refractory period, the process then may advance to optional decision block 172 to confirm the sensing of the far field R wave. More specifically, decision block 172 may be omitted if not considered necessary. If decision block 172 is implemented, the morphology detector 67 determines from digital data stored by the data acquisition system 90 representing the electrogram signal, if the sensed far field R wave is a true far field R wave. As previously described, this morphology confirmation may be implemented through template matching as is known in the art. If in decision block 172 it is determined that a true far field R wave has not been sensed, the process returns to decision block 168. However, if in decision block 172 it is determined that a true far field R wave has been detected, the process then advances to activity block 174 wherein the T wave blanking interval 138 is implemented. As previously mentioned, the T wave blanking interval begins after the far field R wave 124 and extends from before the T wave 126 to a time after the expected T wave. This revised refractory period terminates before or after the original refractory period 130 depending on the location of the far field R wave 124 and the cardiac rate.

In accordance with decision block 176, the rate limit control 65 next determines when the revised refractory period 138 has timed out. When the revised refractory period times out, the process then advances to activity block 178 wherein the minimum RA interval is imposed on the escape interval. As illustrated in FIG. 3, the minimum RA interval 140 begins with the sensing of the far field R wave 124 and terminates at a time thereafter which may be based upon the cardiac or pacing rate. The minimum RA interval is imposed on the escape interval 132 such that if the escape interval 132 is to terminate before the end of the minimum RA interval, the escape interval is extended to end with the ending of the minimum RA interval.

As previously mentioned, both the minimum RA interval and the T wave blanking interval may be determined based upon pacing rate. As the pacing rate increases, these intervals may be shortened. As a result, a maximum pacing rate is imposed for when a patient is both exercising and at rest. When exercising, the maximum pacing rate will be greater than the maximum pacing rate for when the patient is at rest.

While specific embodiments and applications thereof have been described, it is understood that numerous modifications and variations could be made thereto by those skilled in the art without departing from the spirit and scope of the invention.

What is claimed is:

1. In a cardiac stimulation device which paces the atria of a heart on demand at the end of an escape interval in a single-chamber atrial pacing mode, a method of dynamically establishing a maximum pacing rate comprising:
   detecting an atrial activation of the heart;
   detecting an R wave of the heart corresponding to the detected atrial activation;
   determining a minimum RA interval having a beginning that corresponds with the R wave and an end; and
   determining if the end of the escape interval is before the end of the minimum RA interval and if it is, extending the escape interval so that its end coincides with the end of the minimum RA interval.

2. The method of claim 1 further comprising blanking detection during a blanking interval commencing with detection of the atrial activation and ending prior to detection of the R wave.

3. The method of claim 2 further comprising dynamically varying the blanking interval.

4. The method of claim 1 wherein detecting an R wave comprises sensing the R wave with a ventricular electrode configuration.

5. The method of claim 1 wherein the device is a single-chamber atrial pacing device, wherein the R wave is a far field R wave, and wherein detecting the far field R wave comprises sensing with an atrial electrode configuration.

6. The method of claim 1 wherein the device includes a refractory circuit that provides a refractory period following detection of the atrial activation and wherein the method further comprises setting a revised refractory period responsive to detecting the R wave.

7. The method of claim 1 wherein determining comprises determining the minimum RA interval based upon pacing rate.

8. In an implantable cardiac stimulation device which paces the atria of a heart on demand at the end of an escape interval in a single-chamber atrial pacing mode, a system that dynamically establishes a maximum pacing rate comprising:
   a detector that detects an atrial activation of the heart and an R wave of the heart corresponding to the detected atrial activation; and
   a rate limit circuit that determines a minimum RA interval having a beginning that corresponds with the R wave and an end; determines if the end of the escape interval is before the end of the minimum RA interval and if it is, extends the escape interval so that its end coincides with the end of the minimum RA interval.

9. The system of claim 8 further comprising a blanking circuit that disables detection by the detector during a blanking interval commencing with detection of the atrial activation and ending prior to detection of the R wave.

10. The system of claim 9 wherein the blanking interval has a first duration responsive to an intrinsic atrial activation and a second duration responsive to a paced atrial activation.

11. The system of claim 10 wherein the first duration is shorter than the second duration.

12. The system of claim 9 wherein the blanking circuit dynamically varies the blanking interval.

13. The system of claim 8 wherein the device is a single-chamber atrial pacing device, wherein the R wave is a far field R wave, and wherein the detector includes an atrial sense channel that senses the far field R wave.

14. The system of claim 8 wherein the device is a dual-chamber pacing device having a ventricular sense channel and an atrial sense channel and wherein the detector uses the ventricular sense channel to detect the R wave.

15. The system of claim 8 wherein the device includes a refractory circuit that provides a refractory period following detection of the atrial activation and wherein the system further comprises a refractory control that sets a revised refractory period responsive to detection of the R wave.

16. The system of claim 8 wherein the rate limit circuit varies the minimum RA interval responsive to pacing rate.

17. The system of claim 8 further comprising a morphology detector that confirms detection of the R wave.

18. The system of claim 8 further comprising a blanking circuit that disables detection by the detector during a blanking period beginning after the detection of the R wave and ending after a T wave following the R wave.

19. In a cardiac stimulation device which paces the atria of a heart on demand at the end of an escape interval in a single-chamber atrial pacing mode, a system for dynamically establishing a maximum pacing rate comprising:

detecting means for detecting an atrial activation of the heart and an R wave of the heart corresponding to the detected atrial activation; and a rate limit means for determining a minimum RA interval having a beginning that corresponds with the R wave and an end; determining if the end of the escape interval is before the end of the minimum RA interval and if it is, extending the escape interval so that its end coincides with the end of the minimum RA interval.

20. The system of claim 19 further comprising blanking means for disabling detection by the detecting means during a blanking interval commencing with detection of the atrial activation and ending prior to detection of the R wave.

21. The system of claim 20 wherein the blanking means comprises means for dynamically varying the blanking interval.

22. The system of claim 20 wherein the blanking interval has a first duration responsive to an intrinsic atrial activation and a second duration responsive to a paced atrial activation.

23. The system of claim 19 and further comprising a refractory circuit that provides a refractory period following detection of the atrial activation and wherein the system further comprises refractory control means for setting a revised refractory period responsive to detection of the R wave.

* * * * *